(12) United States Patent
Parker

(10) Patent No.: US 8,731,205 B2
(45) Date of Patent: May 20, 2014

(54) BONE CONDUCTION DEVICE FITTING

(75) Inventor: John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 793 days.

(21) Appl. No.: 12/935,905

(22) PCT Filed: Mar. 31, 2009

(86) PCT No.: PCT/US2009/038879
§ 371 (c)(1),
(2), (4) Date: Sep. 30, 2010

(87) PCT Pub. No.: WO2009/124005
PCT Pub. Date: Oct. 8, 2009

(65) Prior Publication Data
US 2011/0026721 A1 Feb. 3, 2011

(51) Int. Cl.
*H04R 29/00* (2006.01)
(52) U.S. Cl.
USPC ............................... 381/59; 381/60; 600/559
(58) Field of Classification Search
USPC .................. 381/59–60, 380; 600/559, 57, 25
See application file for complete search history.

(56) References Cited

U.S. PATENT DOCUMENTS

| | | | |
|---|---|---|---|
| 3,809,829 | A | 5/1974 | Vignini et al. |
| 5,323,468 | A | 6/1994 | Bottesch |
| 5,800,475 | A | 9/1998 | Jules |
| 5,805,571 | A | 9/1998 | Zwan et al. |
| 5,913,815 | A | 6/1999 | Ball et al. |
| 6,496,585 | B1 | 12/2002 | Margolis |

(Continued)

FOREIGN PATENT DOCUMENTS

| | | |
|---|---|---|
| WO | WO 91/12783 | 9/1991 |
| WO | WO 99/07311 | 2/1999 |

(Continued)

OTHER PUBLICATIONS

International Search Report, for PCT/US2009/038879, filed Mar. 31, 2009, mailed May 22, 2009.

(Continued)

*Primary Examiner* — Disler Paul

(57) ABSTRACT

Methods and systems for fitting a bone conduction device are provided herein. These methods and systems comprise determining a gain to be used by the bone conduction device in providing signals at a particular frequency. In determining the gain, a fitting system may provide a test sound that is modulated between a first signal provided to a speaker and a second audible signal provided to a bone conduction device. The first and second audible signal may comprise properties such that when the two signals are added together they produce a constant amplitude output. In an embodiment, each of the first and second audible signals may comprise substantially identical frequency characteristics and signal amplitudes, such as, for example, equal amplitude sinusoids centered on the particular frequency for the measurement. When each of these two audible signals are provided to a recipient of the bone conduction device, the recipient may perceive a variance in the intensity of the sounds when the intensity of the two sounds generated by the two audible signals do not give rise to the same psychophysical loudness. If the recipient perceives this variance, the gain of the bone conduction device may be adjusted to increase or decrease the loudness of the sound provided via the bone conduction device to reduce or eliminate the variance.

19 Claims, 9 Drawing Sheets

(56) References Cited

U.S. PATENT DOCUMENTS

| | | | |
|---|---|---|---|
| 6,602,202 | B2 | 8/2003 | John et al. |
| 6,643,378 | B2 | 11/2003 | Schumaier |
| 6,840,908 | B2 | 1/2005 | Edwards et al. |
| 6,895,345 | B2 * | 5/2005 | Bye et al. .................. 702/57 |
| 7,018,342 | B2 | 3/2006 | Harrison et al. |
| 2004/0028250 | A1 * | 2/2004 | Shim .................. 381/312 |
| 2004/0078057 | A1 | 4/2004 | Gibson |
| 2004/0204921 | A1 | 10/2004 | Bye et al. |
| 2006/0018488 | A1 | 1/2006 | Viala et al. |
| 2006/0287689 | A1 | 12/2006 | Debruyne et al. |
| 2007/0019818 | A1 | 1/2007 | Kurz |
| 2009/0304214 | A1 * | 12/2009 | Xiang et al. .................. 381/307 |
| 2010/0041940 | A1 | 2/2010 | Hillbratt et al. |
| 2011/0022119 | A1 | 1/2011 | Parker |
| 2011/0026748 | A1 | 2/2011 | Parker |

FOREIGN PATENT DOCUMENTS

| | | |
|---|---|---|
| WO | WO 2005/029915 | 3/2005 |
| WO | WO 2007/140367 | 12/2007 |
| WO | WO 2009/124005 | 10/2009 |
| WO | WO 2009/124008 | 10/2009 |
| WO | WO 2009/124010 | 10/2009 |
| WO | WO 2010/017579 | 2/2010 |

OTHER PUBLICATIONS

F.M. Vaneecloo et al., "Réhabilitation prothéétique B.A.H.A des cophoses unilatérales", Annales D'oto-Laryngies et de Chirurgie Cervicofaciale, vol. 117, No. 6, Dec. 2000, pp. 410-417, 8 pages.

Michael Nolan et al., "Transcranial attenuation in bone conduction audiometry", The Journal of Laryngology and Otology, Jun. 1981, vol. 95, pp. 597-608, 12 pages.

European Patent Application No. 02 736 403.3, Office Communication mailed on Oct. 17, 2008. 6 Pages.

European Patent Application No. 02 736 403.3, Office Communication mailed on Apr. 27, 2009. 4 Pages.

European Patent Application No. 02 736 403.3, Office Communication mailed on Apr. 13, 2010. 6 Pages.

International Application No. PCT/SE02/01089, International Search Report mailed on Oct. 1, 2002. 3 Pages.

International Application No. PCT/SE02/01089, International Preliminary Examination Report mailed on Oct. 6, 2003. 5 Pages.

International Search Report issued by the International Searching Authority in connection with International Patent Application No. PCT/AU2009/001010, mailed Nov. 25, 2009 (4 pages).

International Search Report issued by the International Searching Authority in connection with International Patent Application No. PCT/US2009/038879, mailed May 22, 2009 (1 page).

Written Opinion issued by the International Searching Authority in connection with International Patent Application No. PCT/US2009/038879, mailed May 22, 2009 (4 pages).

International Search Report issued by the International Searching Authority in connection with International Patent Application No. PCT/US2009/038884, mailed Jun. 22, 2009.

Written Opinion issued by the International Searching Authority in connection with International Patent Application No. PCT/US2009/038884, mailed Jun. 22, 2009 (5 pages).

Written Opinion issued by the International Searching Authority in connection with International Patent Application No. PCT/US2009/038890, mailed May 29, 2009 (6 pages).

International Preliminary Report on Patentability issued by International Preliminary Examining Authority in connection with International Patent Application No. PCT/US2009/038890, mailed Apr. 15, 2010 (8 pages).

Henry et al., "Bone Conduction: Anatomy, physiology, and Communication." Army Research Laboratory, Aberdeen Proving Ground, MD 21005-5425. May 2007 (206 pages).

* cited by examiner

BONE CONDUCTION DEVICE FITTING

CROSS-REFERENCE TO RELATED APPLICATIONS

The present application is a National Stage Application of International Application No. PCT/US09/38879; filed Mar. 31, 2009, and claims the benefit of U.S. Provisional Patent Application No. 61/041,185; filed Mar. 31, 2008. The contents of these applications is hereby incorporated by reference herein.

BACKGROUND

1. Field of the Invention

The present invention is generally directed to a bone conduction device, and more particularly, to the psychophysical loudness of a bone conduction device.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence or destruction of the hair cells in the cochlea which transduce acoustic signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to provide an electrical stimulus directly to the cochlea nerve, thereby causing a hearing sensation.

Conductive hearing loss occurs when the normal mechanical pathways to provide sound to hair cells in the cochlea are impeded, for example, by damage to the ossicular chain or ear canal. Individuals who suffer from conductive hearing loss may still have some form of residual hearing because the hair cells in the cochlea are generally undamaged.

Individuals who suffer from conductive hearing loss are typically not considered to be candidates for a cochlear implant due to the irreversible nature of the cochlear implant. Specifically, insertion of the electrode array into a recipient's cochlea results in the destruction of a majority of hair cells within the cochlea. This results in the loss of residual hearing by the recipient.

Rather, individuals suffering from conductive hearing loss typically receive an acoustic hearing aid, referred to as a hearing aid herein. Hearing aids rely on principles of air conduction to transmit acoustic signals through the outer and middle ears to the cochlea. In particular, a hearing aid typically uses an arrangement positioned in the recipient's ear canal to amplify a sound received by the outer ear of the recipient. This amplified sound reaches the cochlea and causes motion of the cochlea fluid and stimulation of the cochlea hair cells.

Unfortunately, not all individuals who suffer from conductive hearing loss are able to derive suitable benefit from hearing aids. For example, some individuals are prone to chronic inflammation or infection of the ear canal and cannot wear hearing aids. Other individuals have malformed or absent outer ear and/or ear canals as a result of a birth defect, or as a result of common medical conditions such as Treacher Collins syndrome or Microtia. Furthermore, hearing aids are typically unsuitable for individuals who suffer from mixed hearing losses (i.e., combinations of sensorineural and conductive hearing loss).

When an individual having fully functioning hearing receives an input sound, the sound is transmitted to the cochlea via two primary mechanisms: air conduction and bone conduction. As noted above, hearing aids rely primarily on the principles of air conduction. In contrast, bone conduction devices rely predominantly on vibration of the bones of the recipient's skull to provide acoustic signals to the cochlea.

Those individuals who cannot derive suitable benefit from hearing aids may benefit from bone conduction devices. Bone conduction devices convert a received sound into a mechanical vibration representative of the received sound. This vibration is then transferred to the bone structure of the skull, causing vibration of the recipient's skull. This skull vibration results in motion of the fluid of the cochlea. Hair cells inside the cochlea are responsive to this motion of the cochlear fluid, thereby generating nerve impulses, which result in the perception of the received sound.

SUMMARY

In one aspect of the invention a method for determining the psychophysical loudness of a bone conduction device, at a first frequency, wherein the bone conduction device is worn at a non-functional ear of a recipient having a functional ear is provided. The method comprises: providing a first acoustic signal to the functional ear of the recipient, via a speaker, wherein the first audible signal has the frequency; sending a drive signal to the bone conduction device to cause the bone conduction device to deliver a second audible signal to the recipient at substantially the same time as the first audible signal is delivered, wherein the second audible signal has the first frequency, and wherein the second audible signal is generated using a gain; and adjusting the gain used to generate the second audible signal based on an indication of the recipient's perception of the first and second audible signals.

In a second aspect, a fitting system for determining the psychophysical loudness of a bone conduction device at a first frequency, wherein the bone conduction device is worn at a non-functional ear of a recipient having a functional ear is provided. The system comprises: a speaker configured to provide a first audible signal to the functional ear of the recipient; a bone conduction interface configured to send a drive signal to the bone conduction device to cause the bone conduction device to deliver a second audible signal to the recipient at substantially the same time as the first audible signal is delivered, wherein the second audible signal has the first frequency, and wherein the second audible signal is generated using a gain; and a controller configured to adjust the gain used to generate the second audible signal based on an indication of the recipient's perception of the first and second audible signals.

In a third aspect, a system for determining the psychophysical loudness of a bone conduction device, at a first frequency, wherein the bone conduction device is worn at a non-functional ear of a recipient having a functional ear is provided. The system comprises: means for providing a first acoustic signal to the functional ear of the recipient, via a speaker, wherein the first audible signal has the frequency; means for sending a drive signal to the bone conduction device to cause the bone conduction device to deliver a second audible signal to the recipient at substantially the same time as the first audible signal is delivered, wherein the second audible signal has the first frequency, and wherein the second audible signal is generated using a gain; a means for adjusting the gain used to generate the second audible signal based on an indication of the recipient's perception of the first and second audible signals.

In a forth aspect, there is provided a computer-readable media encoded with instructions operative to cause a computer to perform a method for at least partially fitting a medical implant system to a patient. This method comprises providing to a recipient of a bone conduction device a first audible signal comprising a frequency; providing a second audible signal comprising the frequency to the recipient via the bone conduction device simultaneous with the providing of the first audible signal; and determining a gain of the bone conduction device for the frequency, comprising: adjusting the gain in response to the recipient's perception of the first and second audible signals.

BRIEF DESCRIPTION OF THE DRAWINGS

Embodiments of the present invention are described herein in conjunction with the accompanying drawings, in which.

DETAILED DESCRIPTION

Aspects of the present invention are generally directed to determining the psychophysical loudness of a bone conduction device. Psychophysical loudness refers to the loudness perceived by a recipient in response to a given vibration output of the device. Aspects of the present invention may be advantageously implemented in recipients having one functional cochlea (referred to herein as the good ear) and one non-functioning cochlea (referred to herein as the bad ear). The psychophysical loudness is measured for the recipient by, for example, driving a speaker directed toward the good ear with a first test sound while simultaneously providing a second test sound to the bad ear via the bone conduction device. The first and second test sounds may have substantially identical frequencies, characteristics and amplitudes and are each modulated by a lower frequency sinusoid. The sinusoids modulating the first and second test sounds are identical and 90 degrees out of phase. Thus, if the two test sounds are combined they will produce a constant amplitude sound. If, however, the amplitudes are different, they will produce a warble type sound that may be perceived by the recipient. As used herein, the term "warble" refers to a variance in the intensity in the sound perceived by the recipient, such as, for example, the recipient perceiving a single sound that increases and decreases in loudness.

The two test sounds may be simultaneously played to the recipient. If the recipient indicates that they perceive a warble, the gain of the bone conduction device may be adjusted until the perceived warble disappears. This procedure may be performed at a number of frequencies to generate MAP data comprising a gain versus frequency curves specifying the gain per frequency to be applied by the bone conduction device. This MAP data may be provided to the bone conduction device and used by the bone conduction device in a subsequent stimulation to the recipient.

Figure 1:
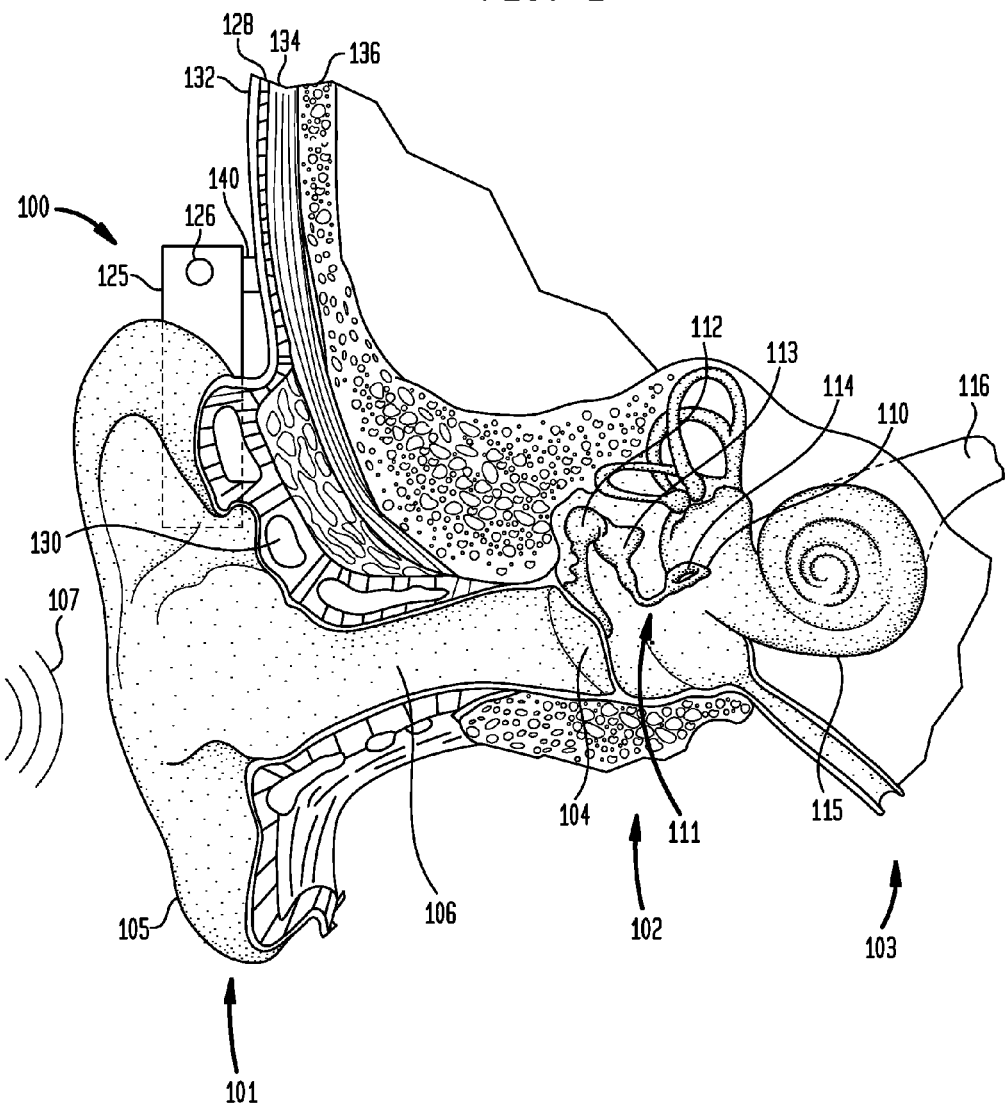
FIG. 1 is a perspective view of a bone conduction device, in which embodiments of the present invention may be advantageously implemented.

FIG. 1 is a cross sectional view of a human ear and surrounding area, along with a side view of one of the embodiments of a bone conduction device 100. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. The motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 may be positioned behind outer ear 101 of the recipient; however it is noted that device 100 may be positioned in any suitable manner.

In the embodiments illustrated in FIG. 1, bone conduction device 100 comprises a housing 125 having at least one microphone 126 positioned therein or thereon. Housing 125 is coupled to the body of the recipient via coupling 140. As described below, bone conduction device 100 may comprise a signal processor, a transducer, transducer drive components and/or various other electronic circuits/devices.

In accordance with embodiments of the present invention, an anchor system (not shown) may be implanted in the recipient. As described below, the anchor system may be fixed to bone 136. In various embodiments, the anchor system may be implanted under skin 132 within muscle 134 and/or fat 128 or the hearing device may be anchored in another suitable manner. In certain embodiments, a coupling 140 attaches device 100 to the anchor system.

Figure 2A:
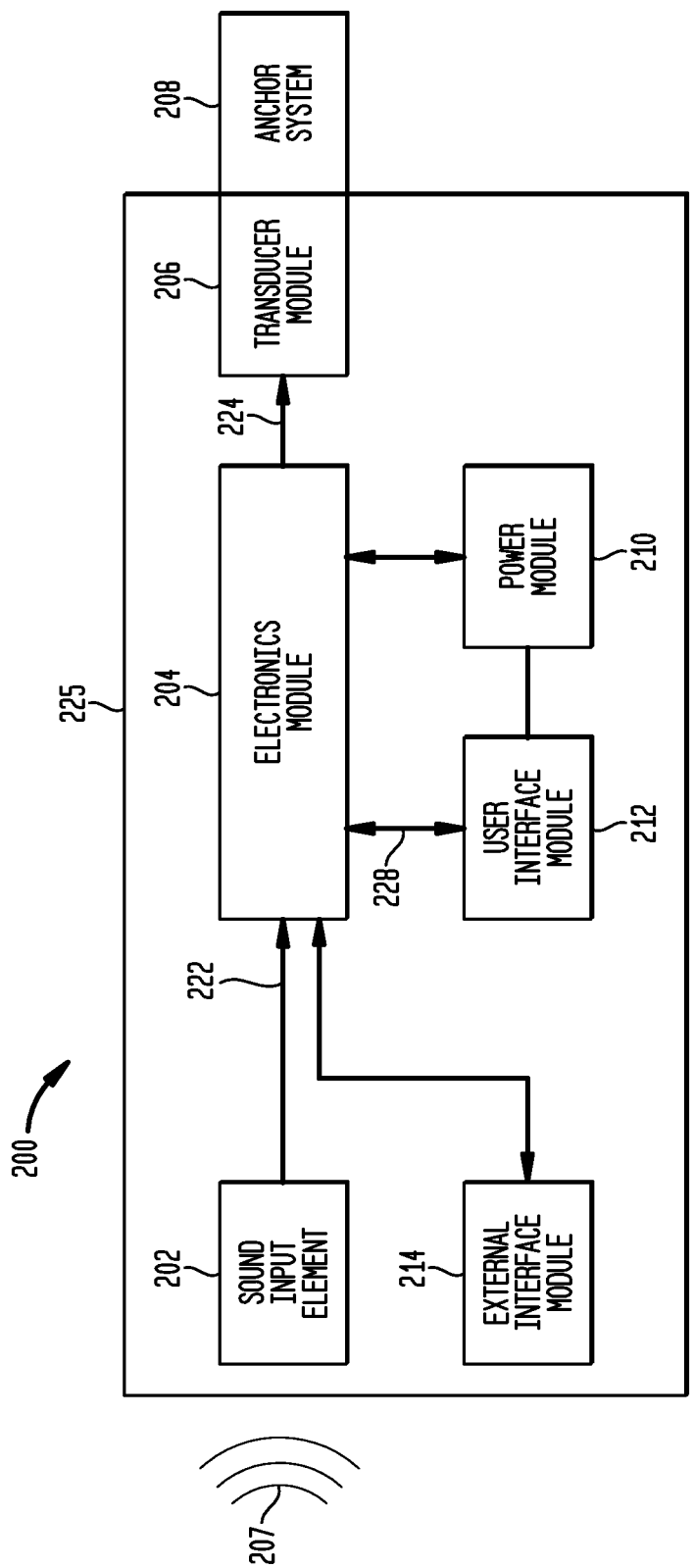
FIG. 2A is a high-level functional block diagram of a bone conduction device, such as the bone conduction device of FIG. 1, in accordance with embodiments of the present invention.

A functional block diagram of one embodiment of bone conduction 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As shown in FIG. 2A, a transducer 206 receives adjusted electrical signal 224 and generates a mechanical output force that is delivered to the skull of the recipient via an anchor system 208 coupled to bone conduction device 200. Delivery of this output force causes one or more of motion or vibration of the recipient's skull, thereby activating the hair cells in the cochlea via cochlea fluid motion.

FIG. 2A also illustrates a power module 210. Power module 210 provides electrical power to one or more components of bone conduction device 200. For ease of illustration, power module 210 has been shown connected only to user interface module 212 and electronics module 204. However, it should be appreciated that power module 210 may be used to supply power to any electrically powered circuits/components of bone conduction device 200.

Bone conduction device 200 further includes a user interface module 212 that allows the recipient to interact with device 200. For example, user interface module 212 may allow the recipient to adjust the gain of the bone conduction device 200, alter the speech processing strategies, power on/off the device, etc. User interface module 212 communicates with electronics module 204 via signal line 228.

Bone conduction device 200 may further include an external interface module 214 that may be used to connect electronics module 204 to an external device, such as a fitting system. Using external interface module 214, the external device, may obtain information from the bone conduction device (e.g., the current parameters, data, alarms, etc.) and/or modify the parameters of the bone conduction device 200 used in processing received sounds.

In the embodiment illustrated in FIG. 2A, sound input element 202, electronics module 204, transducer 206, power module 210, user interface module 212, and external interface module 214 been shown as integrated in a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

Figure 2B:
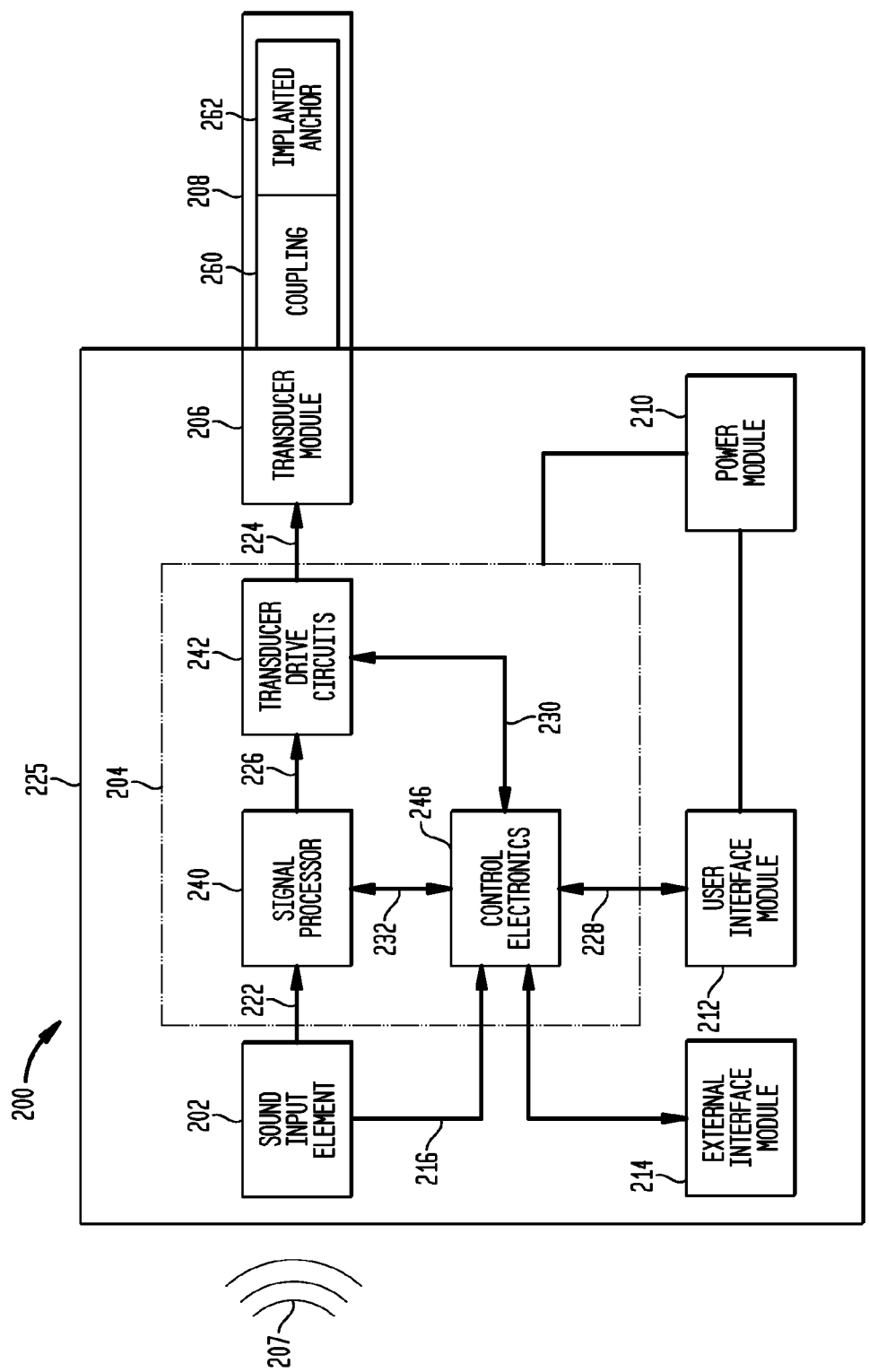
FIG. 2B is detailed functional block diagram of the bone conduction device illustrated in FIG. 2A in accordance with embodiments of the present invention.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 224A. In certain embodiments, sound processor 240 may comprise substantially the same sound processor as is used in an air conduction hearing aid. In further embodiments, sound processor 240 comprises a digital signal processor.

Processed signal 226A is provided to transducer drive components 242. Transducer drive components 242 output a drive signal 224B, to transducer 206. Based on drive signal 224B, transducer 206 provides the output force to the skull of the recipient. For ease of description, the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, anchor system 208 comprises a coupling 260 and an implanted anchor 262. Coupling 260 may be attached to one or more of transducer 206 or housing 225. For example, in certain embodiments, coupling 260 is attached to transducer 206 and vibration is applied directly thereto. In other embodiments, coupling 260 is attached to housing 225 and vibration is applied from transducer 206 through housing 225.

As shown in FIG. 2B, coupling 260 is coupled to an anchor implanted in the recipient, referred to as implanted anchor 262. As explained with reference to FIG. 3, implanted anchor 262 provides an element that transfers the vibration from coupling 260 to the skull of the recipient.

As shown, control electronics 246 may be connected to one or more of user interface module 212, external interface module 214, sound input element 202, sound processor 240 and/or transducer drive components 242. In embodiments, based on inputs received at user interface module 212 or external interface module 214, control electronics 246 may provide instructions to, or request information from, other components of bone conduction device 200.

As noted above, a recipient may control various functions of the device via user interface module 212. User interface module 212 includes one or more components that allow the recipient to provide inputs to, or receive information from, elements of bone conduction device 200. Further, as noted above, external interface module 214 may be used to connect electronics module 204 to an external device, such as a fitting system. Using external interface module 214, a fitting system may be able to obtain and/or modify information for the various components of bone conduction device 200. For example, in an embodiment, a fitting system may use external interface module 214 to obtain and modify the parameters of sound processor 240 used in processing, amplifying, and filtering the received sound. External interface module 214 may comprise a plug for permitting a wired connection between bone conduction device and an external device, or, for example, wireless communications hardware and/or software to permit a wireless connection between bone conduction device and an external device. Such a wireless connection may use any appropriate wireless mechanism, such as, for example, Wi-Fi (IEEE 802.11), Bluetooth, etc.

Figure 3:
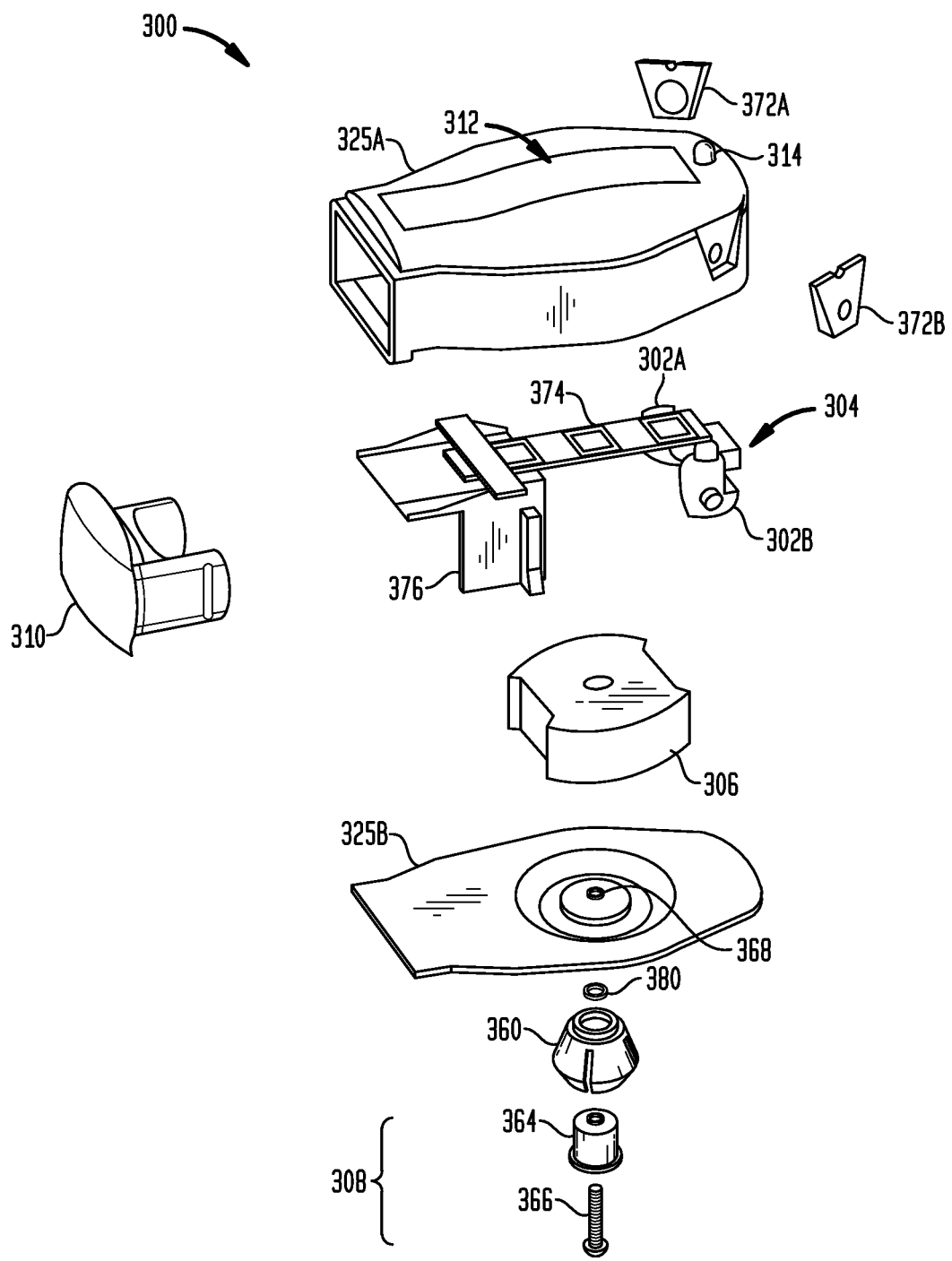
FIG. 3 is an exploded view of the bone conduction device illustrated in FIG. 1, in accordance with embodiments of the present invention.

FIG. 3 illustrates an exploded view of one embodiment of bone conduction 200 of FIGS. 2A and 2B, referred to herein as bone conduction device 300. As shown, bone conduction device 300 comprises an embodiment of electronics module 204, referred to as electronics module 304. As explained above, electronics module 304 may include a sound processor, transducer drive components and control electronics. These components may be separate components or included in a single component (e.g., a microprocessor, application specific integrated circuit (ASIC), etc.).

In the illustrated embodiment, electronics module 304 includes a printed circuit board 374 (PCB) to electrically connect and mechanically support the components of electronics module 304. Attached to PCB 374 are one or more sound input elements, shown as microphones 302 to receive a sound.

In the illustrated embodiment, bone conduction device 300 further comprises battery shoe 310 for supplying power to components of device 300. Battery shoe 310 may include one or more batteries. In certain embodiments, PCB 374 is attached to a connector 376. Connector 376 is configured to mate with battery shoe 310. In certain embodiments, connector 376 and battery shoe 310 may be releasably snap-locked to one another. Furthermore, in such embodiments, one or more battery connects (not shown) are disposed in connector 376 to electrically connect battery shoe 310 with electronics module 304.

In the embodiment illustrated in FIG. 3, bone conduction device 300 further includes a two-part housing 325, comprising first housing portion 325A and second housing portion 325B. Housing portions 325 are configured to mate with one another to substantially seal bone conduction device 300.

In the embodiment of FIG. 3, first housing portion 325A has an opening therein for receiving battery shoe 310. In such embodiments, battery shoe protrudes through first housing portion 325A and may be removed or inserted by the recipient. Also in the illustrated embodiment, microphone covers 372 are releasably attached to first housing portion 325A. Microphone covers 372 provide a barrier over microphones 302 to protect microphones 302 from dust, dirt or other debris.

Bone conduction device 300 further includes an embodiment of user interface module 212, referred to herein as user interface module 312. User interface module 312 is configured to provide or receive user inputs from the recipient.

Also as shown in FIG. 3, bone conduction device 300 comprises an embodiment of transducer 206, referred to as transducer 306. Transducer 306 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, bone conduction device 300 delivers the output force to the skull of the recipient via an anchor system 308. Anchor system 308 comprises a coupling 360 and implanted anchor 362. In the embodiment illustrated in FIG. 3, coupling 360 is configured to be attached to second housing portion 325B. As such, in this embodiment, vibration from transducer 306 is provided to coupling 360 through housing 325B. In the embodiment shown in FIG. 3, an opening 368 is provided in second housing portion 325B. A screw (not shown) may be inserted through opening 368 to attach transducer 306 to coupling 360. In such embodiments, an O-ring 380 may be provided to seal opening 368 around the screw.

As noted above, anchor system 308 includes implanted anchor 362. Implanted anchor 362 comprises a bone screw 366 implanted in the skull of the recipient and an abutment 364. In an implanted configuration, screw 366 protrudes from the recipient's skull through the skin. Abutment 364 is attached to screw 366 above the recipient's skin. In other embodiments, abutment 364 and screw 366 may be integrated into a single implantable component. Coupling 360 is configured to be releasably attached to abutment 364 to create a vibratory pathway between transducer 306 and the skull of the recipient.

Bone conduction device 300 further includes an embodiment of external interface module 214, referred to herein as external interface module 314. External interface module 314 may include a jack connector for receiving a plug for a wired connection to an external device. Or, for example, external interface module 314 may comprise hardware and/or software for wirelessly connecting to an external device.

In alternative embodiments of the present invention, bone conduction device 300 may comprise one or more additional sound input elements. For example, bone conduction device 300 may comprise an electrical input 316. In such embodiments, the electrical input is configured to connect device 300 to external equipment and receive an electrical sound signal directly therefrom. Electrical input 316 may permit bone conduction device 300 to be connected to, for example, FM hearing systems, MP3 players, televisions, mobile phones, etc.

In still other embodiments, a further sound input element in the form of a telecoil 318 may be integrated in, or connected to, bone conduction device 300. Telecoil 318 permits bone conduction device 300 to receive input signals from, for example, a telephone or other similar device.

Figure 4:
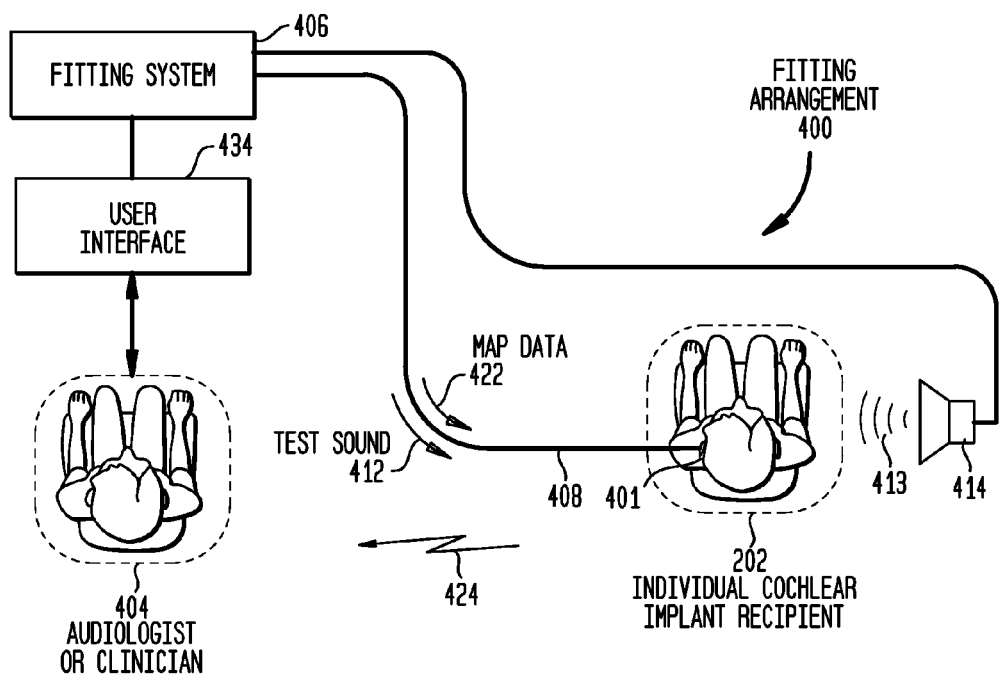
FIG. 4 is a schematic diagram illustrating one exemplary arrangement in which a fitting system may be implemented for use in determining the bone conduction device's psychophysical loundness, in accordance with embodiments of the present invention.

As noted above, in embodiments, the psychophysical loudness of the bone conduction device may determined and this psychophysical loudness used in processing the acoustic signals. FIG. 4 is a schematic diagram of an exemplary fitting arrangement 400 in which a fitting system 406 may be implemented for use in fitting a bone conduction device 401. As will be discussed in more detail below, fitting arrangement 400, in fitting bone conduction device 401, may determine the bone conduction device's psychophysical loudness. As noted above, the psychophysical loudness of the bone conduction device refers to the loudness perceived by the recipient 402 to a given vibration output. As illustrated, fitting arrangement 400 may comprise a fitting system 406 that an audiologist 404 may use, a speaker 414, a bone conduction device 401 fitted to a recipient 402, a data communication link 408 connecting fitting system 406 to bone conduction device 401, and a user interface 434.

An audiologist 404 may use fitting system 406 to create individualized recipient MAP data 422 that is to be used for subsequent operations by bone conduction device 401. This MAP data 422 may comprise individualized programs, commands, data, settings, parameters, instructions, and/or other information (generally and collectively referred to as a "MAP data" herein) that define the specific characteristics used by the bone conduction device 401 in applying stimulation to the recipient 402. After determining the MAP data, fitting system 406 may digitally store the MAP data on system 406 and ultimately download the MAP data 422 to the memory of electronics module 204 of bone conduction device 401.

In an embodiment, fitting system 406 may comprise, for example, computer hardware and software, including, for example, one or more interfaces for connecting to a speaker 414, bone conduction device 401, a display device (e.g., monitor), and a user input device(s) (e.g., keyboard, mouse, touchscreen, etc.). A more detailed description of an exemplary fitting system is provided below with regards to FIG. 8.

Audiologist 404 may be, for example, any person operating fitting system 406 whether an audiologist, clinician, or any other person. Speaker 414 may be any type of device configured to convert electrical or other signals to sound, such as, for example, a loudspeaker, a headphone, an earphone, etc.

User interface 334 may comprise any device which may be used by audiologist 404 to communicate with fitting system 206. For example, user interface 334 may comprise a display device for displaying information from fitting system 406 to audiologist 404. Exemplary display devices include, for example, a computer monitor, touch screen device, etc. Additionally, user interface 334 may comprise one or more input devices for enabling audiologist 402 to provide information, such as instructions or data, to fitting system 206. Exemplary input devices include a computer keyboard, mouse, voice-responsive software, touch-screen, retinal control, joystick, and any other data entry or data presentation formats now or later developed.

Recipient 402 may have one ear with a functional cochlea (e.g., the recipient experiences normal hearing with this "good ear") and one ear suffering from conductive hearing loss (referred to herein as the "bad ear"). In the exemplary arrangement 400, a bone conduction device 401 may be implanted adjacent to the bad ear, and fitted to the recipient's bad ear. A speaker 414 of fitting system 406 may be directed toward the good ear. Bone conduction device 401 may be fitted in a manner, such as, for example, as was described above with reference to FIG. 1. Speaker 414 may be, for example, a loudspeaker placed a particular distance away from the good ear (e.g., 1 meter) and directed towards the good ear. Or, for example, speaker 414 may be embodied in a earpiece attached to the recipient's good ear.

Figure 5:
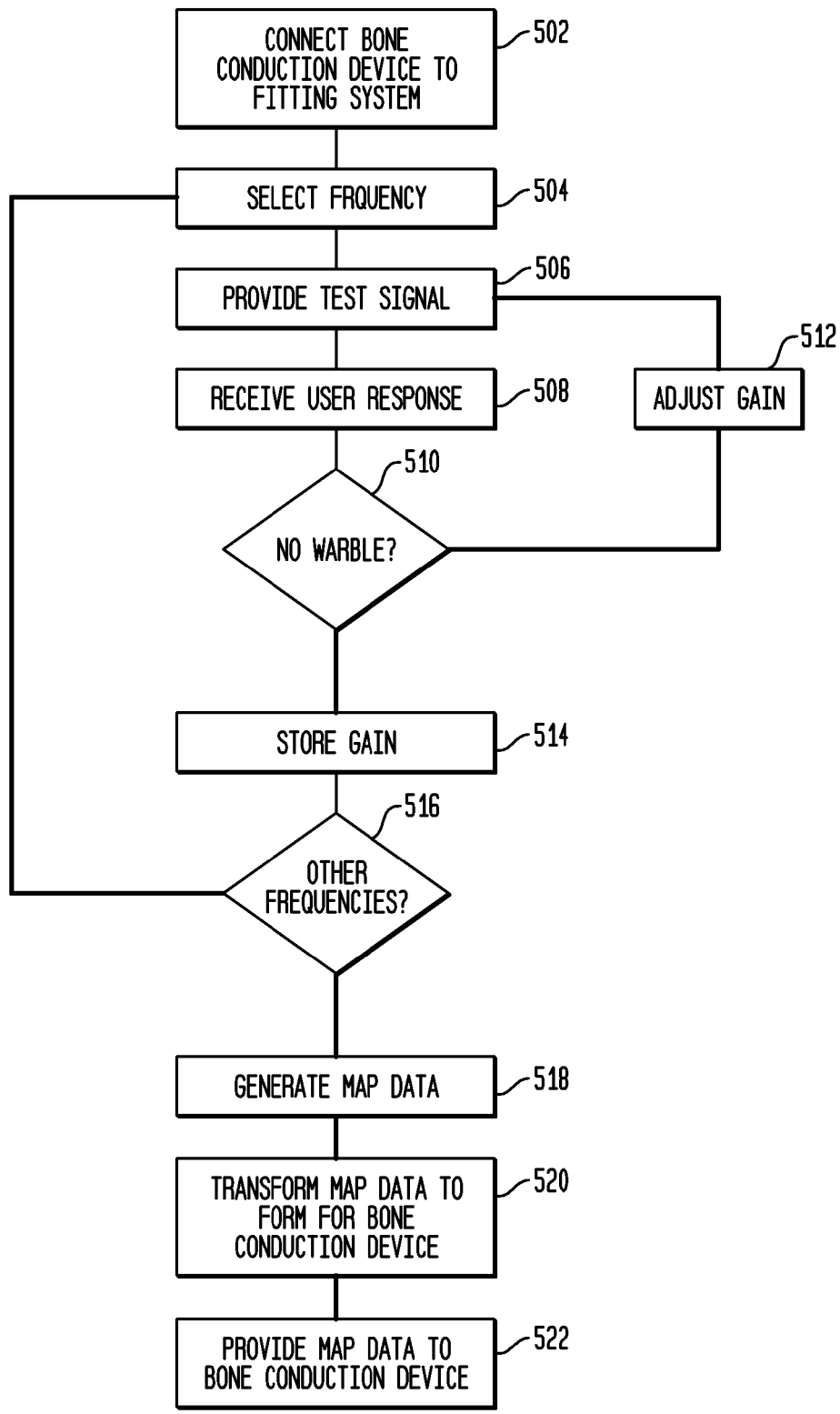
FIG. 5 is a high-level flow chart illustrating operations that may be performed to measure the psychophysical loudness of a bone conduction device, in accordance with embodiments of the present invention.

FIG. 5 is a high-level flow chart illustrating operations that may be performed to measure the psychophysical loudness of a bone conduction device. Process 500 is described below with reference to the fitting system illustrated in FIG. 4 although any bone conduction device may be utilized in the implementation of embodiments of the present invention.

At block 502 bone conduction device 401 may be connected to fitting system 406 to establish a data communication link 408 between the bone conduction device 401 and fitting system 406. System 406 is thereafter bi-directionally coupled with bone conduction device 401 via data communication link 408. It should be appreciated that although bone conduction device 401 and fitting system 406 are connected via a cable in FIG. 4, any communications link now or later developed may be utilized to communicably couple the implant and fitting system.

After connecting fitting system 406 and bone conduction device 401, fitting system 406 selects one or more frequencies at block 504 for measuring the bone conduction device's psychophysical loudness at the selected frequency/ies. The selected frequency/ies may be, for example, selected from a set of frequencies for which the fitting system is to determine a corresponding gain of the bone conduction device. Such a set of frequencies may be stored in fitting system 406 and/or provided to fitting system 406 by the audiologist 404 using, for example, a user interface 434.

Fitting system 406 may then, at block 506, apply test signals at the selected frequency/ies. Fitting system 406 may apply the test signals by, for example, transmitting signals for one or more test sounds to bone conduction device 401 and speaker 414, respectively. Speaker 414 emits the acoustic test sound 413 in accordance with signal from fitting system 406 for test sound 413, and bone conduction device 401 applies vibration in accordance with test sound 412. The properties of test sounds 413 and 412 may be such that when the two sounds are added together, they result in a constant intensity. For example, test sounds 413 and 412 may be such that when both are presented to recipient 402, the recipient will perceive a constant intensity sound if the psychological loudness of the two sounds are equal and a warble in the intensity when the two test sounds 413 and 412 do not give rise to the same psychophysical loudness.

The amplitude of the provided test signals may be equal and provided so that the recipient's perception of the acoustic test sound is between the threshold level (also referred to as a "T-Level") and a maximum comfort level (also referred to as a "C-Level") for the recipient (i.e., the sound from the speaker is loud enough to be heard by the recipient but not so loud that it is uncomfortable to the recipient). Thus, in an embodiment, the two provided test sounds may have equal amplitudes when they arrive at the recipient's ear and bone conduction device, respectively. However, due to attenuation across the skull of the vibrations from the bone conduction device and the gain applied by the bone conduction device, the psychophysical loudness of the two sounds as perceived by the recipient may be different.

Test sounds 413 and 412 may have identical frequency characteristics. For example, test sounds 413 and 412 may each be a pure tone at a single frequency or a very narrow band of frequencies. In some embodiments, test sounds 413 and 412 are generated from a common sinusoid at a particular frequency that is then modulated between bone conduction device 401 and speaker 414. In other embodiments, test sounds 413 and 412 are more complex sounds, such as, for example, noise centered on the selected frequency which is modulated between bone conduction device 401 and speaker 414.

In certain embodiments, test sounds 413 and 412 have the same amplitude when provided to recipient 402 and may be the identical waveform, with the exception that they are 90 degrees out of phase. Bone conduction device 401 may apply a variable gain to test sound 412. Thus, the intensity of the vibrations from bone conduction device 401 (and accordingly the psychophysical loudness of the corresponding perceived sound) resulting from test sound 412 may vary depending on the amount of gain applied.

Initially the gain applied by bone conduction device 401 may be set to a default amount. If the gain is properly set, the psychophysical loudness of the test sounds 413 and 412 will constructively combine to produce a constant amplitude sound at the selected frequency. If, however, the gain is not properly set, the psychophysical loudness of the test sounds 413 and 412 will be different, and the recipient 402 may perceive a warble.

Figure 6A:
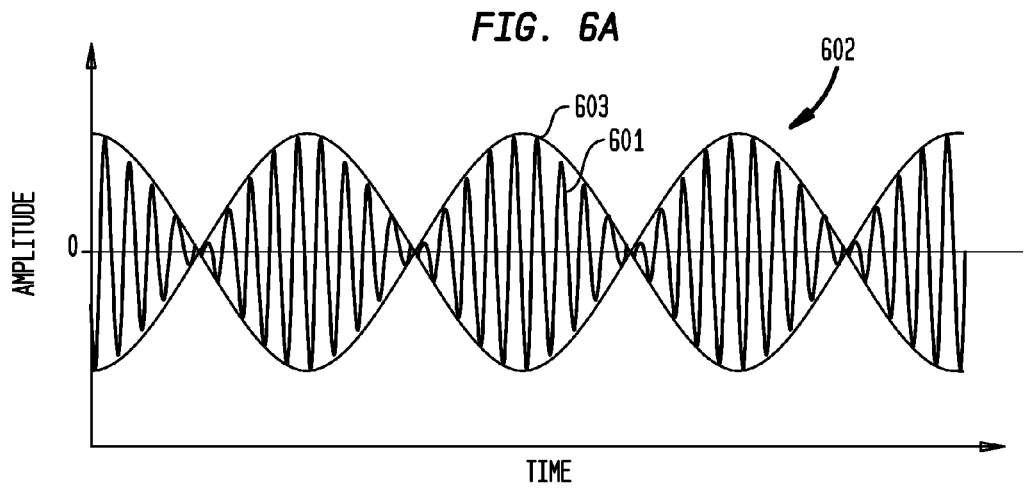
FIG. 6A illustrates an exemplary test sound in which a sound sinusoid is modulated by slower modulation sinusoid, in accordance with embodiments of the present invention.
Figure 6B:
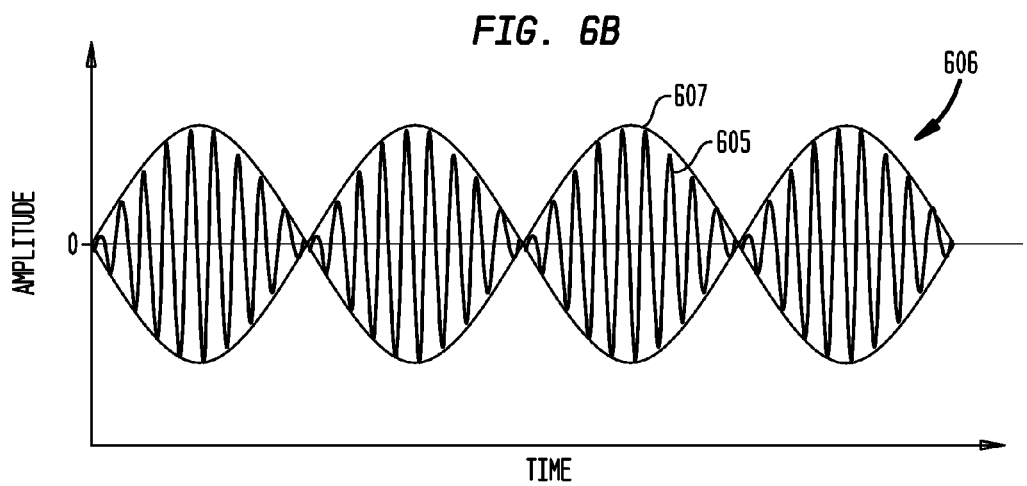
FIG. 6B illustrates a test sound comprising a sound sinusoid modulated by slower modulation sinusoid, in accordance with embodiments of the present invention.
Figure 6C:
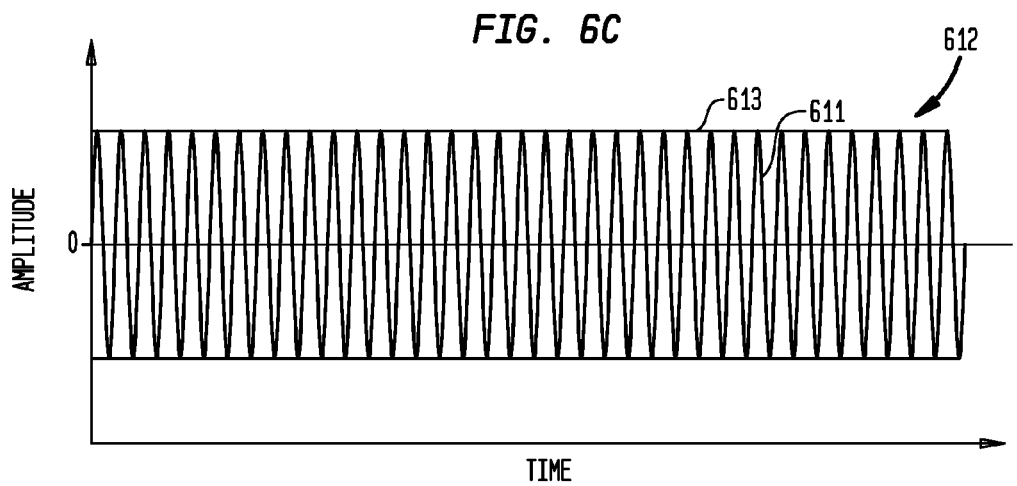
FIG. 6C illustrates a combined signal resulting from combining sound signals, in accordance with embodiments of the present invention.

FIGS. 6A-C and 7A-C will now be described to provide an illustrative example of how a constant amplitude sound may be perceived if the psychophysical loudness of two out-of-phase sounds are the same; and, how a warble may be perceived if the psychophysical loudness from the two sounds is different. FIGS. 6A-C illustrate exemplary test sound signals that when combined produce a constant output intensity, in accordance with an embodiment. FIG. 6A illustrates an exemplary test sound 602 in which a sound sinusoid 601 is modulated by slower modulation sinusoid 603. Sound sinusoid 601 may comprise a frequency in the audible frequency range (e.g., 20 Hz-20 kHz), such as, for example 60 Hz, 10 kHz, etc. Modulation sinusoid may have a slower frequency, such as for example, a frequency of less than 20 Hz. Thus, test sound 602 may present a sound to the recipient 402 at the frequency of sound sinusoid 601, but increasing and decreasing in loudness in accordance with modulation sinusoid 603. Similarly, FIG. 6B illustrates a test sound 606 comprising a sound sinusoid 605 modulated by slower modulation sinusoid 607. Sound sinusoid 605 and modulation sinusoid 607 may be identical to sound sinusoid 606 and modulation sinusoid 607, with the exception that modulation sinusoid 607 is 90 degrees out of phase with modulation sinusoid 603. Further, in embodiments, sound sinusoids 601 and 605 may be the same signal, but modulated such that the sound sinusoid shifts between test sounds 602 and 606. Further, as illustrated, sound signal 602 and sound signal 604 have the same amplitudes.

FIG. 6C illustrates a combined signal 612 resulting from combining sound signals 602 and 606. As illustrated, combined signal 612 is a constant amplitude 611 sinusoid 613. Thus, when combined, recipient 402 may perceive a constant amplitude sound at the frequency corresponding to the sound sinusoids 601 and 605.

Figure 7A:
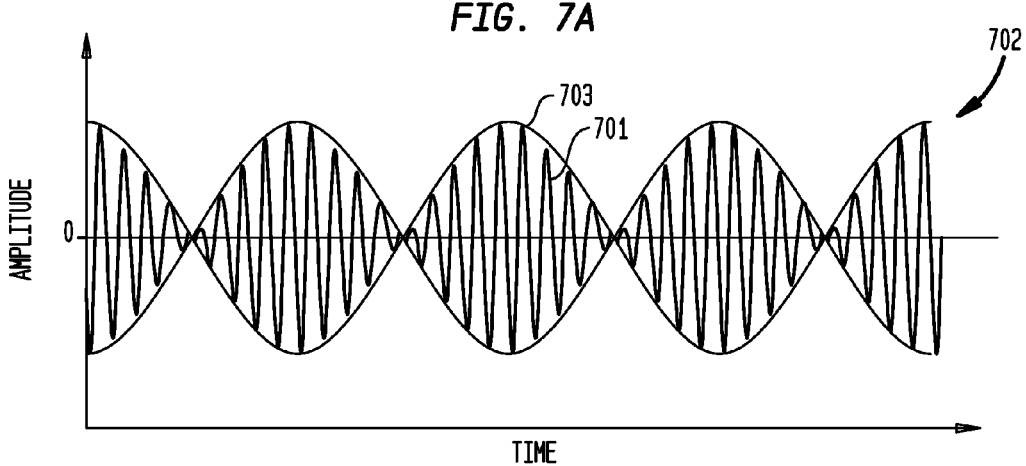
FIG. 7A illustrates an exemplary test sound in which a sound sinusoid is modulated by slower modulation sinusoid, in accordance with embodiments of the present invention.
Figure 7B:
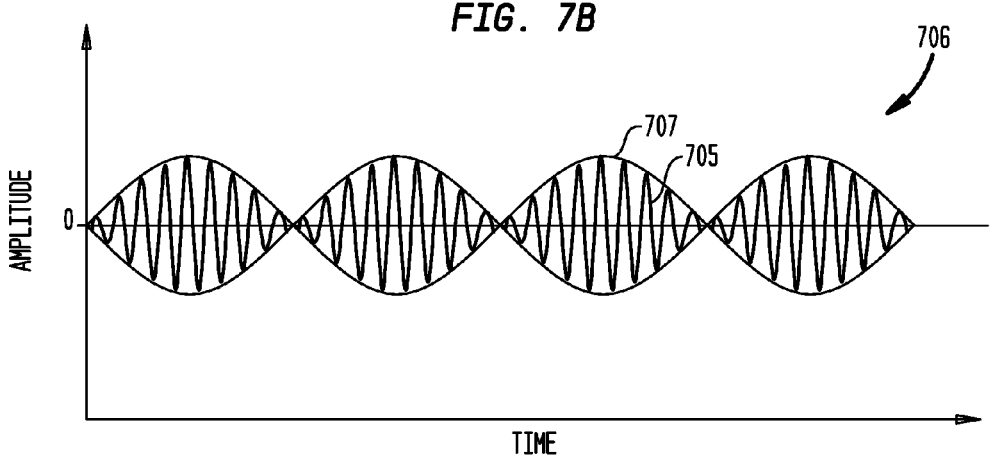
FIG. 7B illustrates a test sound comprising a sound sinusoid modulated by slower modulation sinusoid, in accordance with embodiments of the present invention.
Figure 7C:
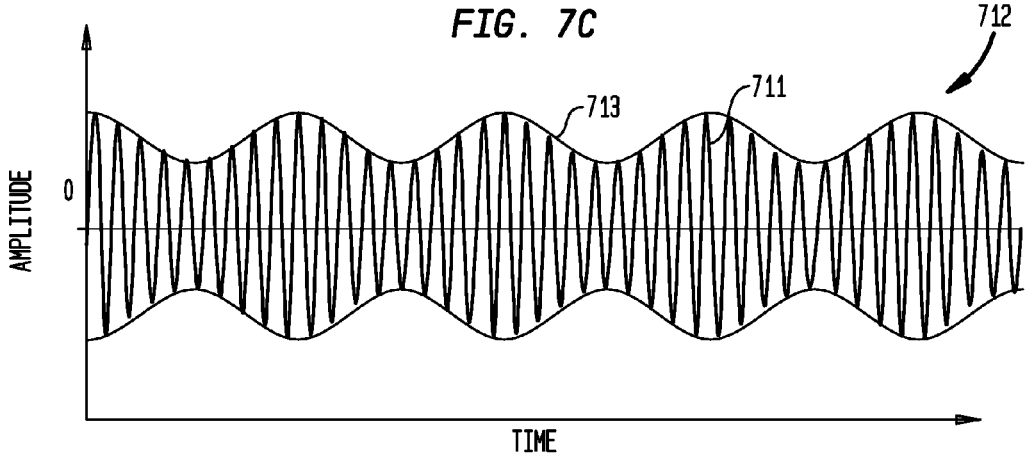
FIG. 7C illustrates a combined signal resulting from combining sound signals, in accordance with embodiments of the present invention.

FIGS. 7A-C illustrate exemplary test sound signals where the test sounds have different amplitudes, in accordance with an embodiment. These test sounds are identical to the test sounds of FIGS. 6A-6C with the exception that the test sounds FIGS. 7A-C have different amplitudes. As will be discussed below, this difference in amplitudes, may result in the recipient 402 perceiving a warble in response to listening to the combined signals.

As with FIG. 6A, FIG. 7A illustrates an exemplary test sound 702 in which a sound sinusoid 701 is modulated by slower modulation sinusoid 703. Test sound 702, sound sinusoid 701 and modulation sinusoid 703 may be identical to test sound 602, sound sinusoid 601 and modulation sinusoid 603, respectively, of FIG. 6A. Similarly, FIG. 7B illustrates a test sound 706 comprising a sound sinusoid 705 modulated by slower modulation sinusoid 707. Test sound 706 may be identical to test sound 606 of FIG. 6B with the exception that, as illustrated, test sound 706 has a lower amplitude than test sound 606. Test sound 706 may have a lower amplitude than test sound 606 due to, for example, the bone conduction device 401 having a lower gain setting during application of test sound 706 than during application of test sound 606.

FIG. 7C illustrates a combined signal 712 resulting from combining sound signals 702 and 706. As illustrated, combined signal 712 is a sinusoid 713 that varies in amplitude 713 due to the differences in amplitudes between test sounds 702 and 706. This variance in amplitude may be perceived as a warble by the recipient 402.

Referring back to FIG. 5, after providing the test signals, the audiologist 404 may obtain the recipient's response at block 508. If the recipient perceives a warble, at decision 510, the gain of the bone conduction device may be adjusted at block 512. The gain may be adjusted by, for example, the recipient 402 or audiologist 404. In an embodiment, recipient 402 may provide feedback 424 to audiologist 404 who may adjust the gain of bone conduction device 401 based on the feedback 424. This feedback 424 may be provided, for example, by the recipient telling the audiologist 404 whether or not a warble was perceived. Audiologist 404 may adjust the gain using user interface 434, which then may send an instruction to bone conduction device 401 to adjust the gain. Or, for example, the recipient 402 may be able to adjust the gain themselves by, for example, adjusting a dial to increase or decrease the gain of bone conduction device 401. This dial may be, included in bone conduction device 401, or, for example, in a separate device that may be able to communicate with bone conduction device 401 in adjusting the gain. Such an external device may communicate directly with bone conduction device 401 via a wired or wireless connection. Or, for example, such an external device may communicate with fitting system 406, and, in response, fitting system 406 adjusts the gain of bone conduction device 401. In such embodiments, the user response received at block 508 may simply be an adjustment in the gain by the recipient, and the decision at block 510 may be simply a determination by the recipient 402 regarding whether or not they still perceive a warble. Then, when the recipient 402 perceives that the warble has been sufficiently reduced (e.g., eliminated), the recipient 402 may provide an indication regarding such to the audiologist 404 at block 508 that may then provide this indication to fitting system 406. Accordingly, blocks 506 508, and 512 may be repeated until the bone conduction device's gain is adjusted such that recipient 402 no longer perceives a warble at decision 510 indicative of the psychophysical loudness of test sounds 413 and 412 being the same.

Fitting system 406 may then store this determined gain at block 512 in, for example, a storage (e.g., memory) of fitting system 406. In an embodiment, fitting system 406 may obtain this determined gain directly from the bone conduction device 401 after the warble has been eliminated. Or, for example, audiologist 404 may provide this determined gain to the fitting system 406 by, for example, reading a display or other visible indication on the bone conduction device 401 or other device indicating the gain of the bone conduction device 401.

Next, fitting system 406 may determine whether the gains for additional frequencies should be determined at decision 514. This determination may be made, for example, by audiologist 404 providing instructions to fitting system 406 regarding the number and specifics of the frequencies for fitting system 406 to determine gains. Or, for example, the number and specifics of the frequencies for which gains are to be measured may be stored in fitting system 406.

If fitting system 406 is to determine gains for additional frequencies, the process returns to block 504, sets the frequency to the next frequency and repeats blocks 506-514 to determine the gain for these additional frequencies. After fitting system 406 determines the gains for all the specified frequencies, the process proceeds to block 516 and fitting system generates MAP data in accordance with the measured gains. In an embodiment, this MAP data may comprise a gain versus frequency curve specifying the gain per frequency to be applied by bone conduction device 401 in providing stimulation to recipient 402. In an embodiment, fitting system 406 may determine the gains for a subset of frequencies representative of the frequency range of bone conduction device 401. Then, fitting system 406 may, at block 516, fit a curve to these measured gains. This may be accomplished, for example, by fitting system 406 linearly interpolating the gains between measured gains, or for example, fitting a pre-determined curve shape to the measured gains.

At block 518, fitting system 406 may transform the MAP data (e.g., the determined gain versus frequency curve) from the fitting system's domain to the domain of the bone conduction device 401. The MAP data 422 may downloaded from fitting system 406 to bone conduction device 401 at block 520. The bone conduction device 401 may then use the provided MAP data in applying stimulation at block 522.

In a further embodiment, fitting system 406 may determine the gains for a plurality of amplitudes of the test signals for each frequency. For example, a gain may be measured for a particular frequency where the sound provided from the speaker arriving at the recipient's ear is at 40 dB. Then, another gain may be measured for this particular frequency, but where the sound provided from the speaker arriving at the recipient's ear is at 100 dB. The fitting system may then determine the gain to be used for this frequency by, for example, averaging the measured gains for the frequency.

Figure 8:
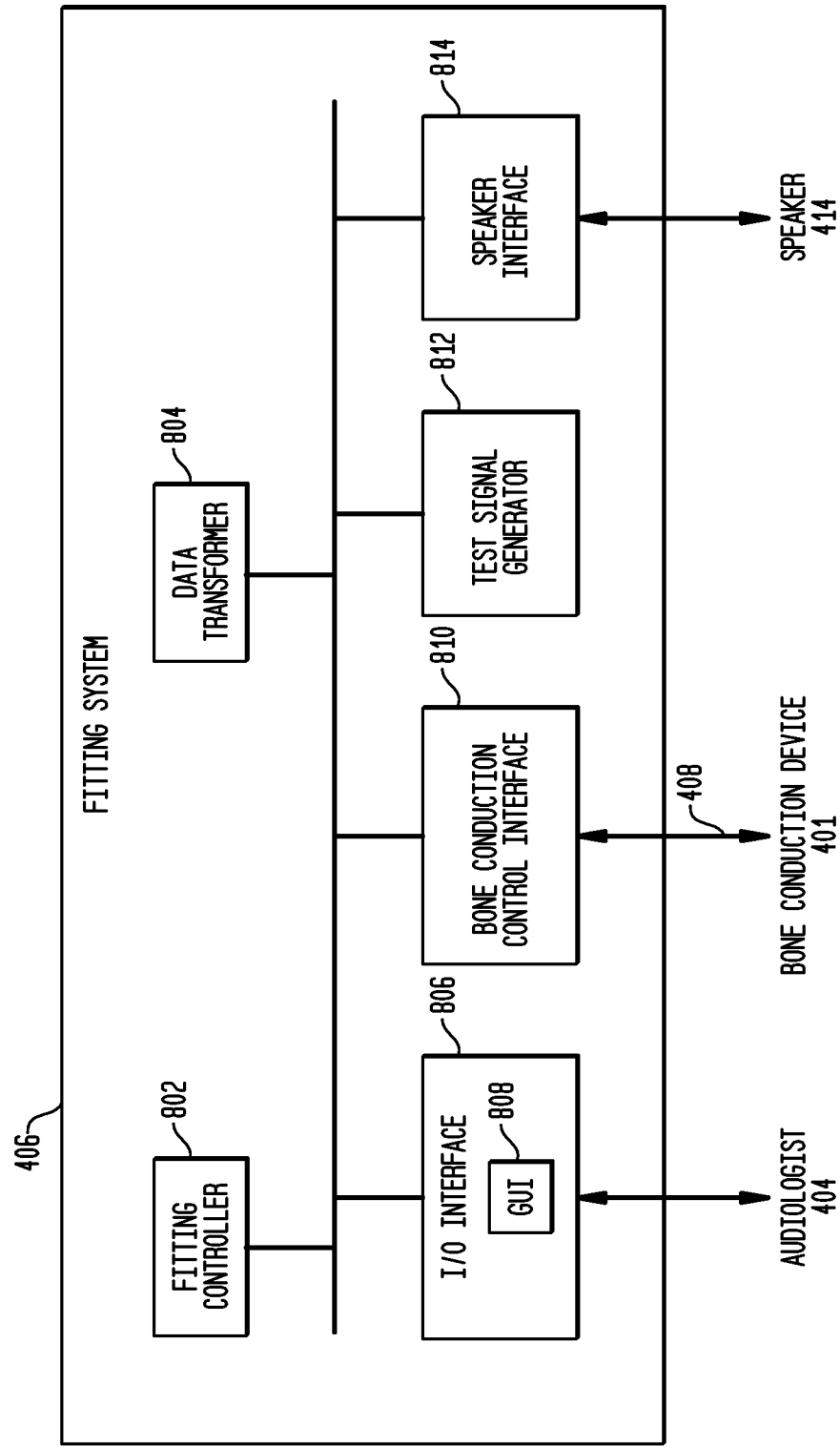
FIG. 8 is a high-level functional block diagram of a fitting system 406, in accordance with embodiments of the present invention.

FIG. 8 is a high-level functional block diagram of a fitting system 406 according to an embodiment. The primary components and operative aspects of fitting system 406 are shown in block diagram form for ease of description, and are described herein. As illustrated, the components may be coupled by a communications bus. However, it is to be understood that the components of fitting system 406 may be connected in any manner suitable for the particular application. Additionally, these components may be software functions executed by a processor. It should be noted that these functions are illustrated as separate functional blocks for explanatory purposes, and in implementation the functions may be combined in other manners.

As illustrated, fitting system 406 may comprise a fitting controller 802, a data transformer 804, an input/output interface 806, a bone conduction control interface 810, a test signal generator 812, and a speaker interface 814. Fitting controller 802 may control the other components of fitting system 406 and control the operations of the fitting process. Bone conduction control interface 810 may be used to send test signals and information, such as MAP data 422 and instructions, to bone conduction device 401 via data communication link 408.

Test signal generator 812 may generate test signals 413 and 412. Test signal 413 may be sent to bone conduction device 401 via bone conduction interface 810 and test signal 412 may be sent to speaker 414 via speaker interface 814. Speaker interface 814 may be any type of interface capable of sending sound signals to a speaker, such as, for example, a headphone jack, an RCA interface, an optical interface, etc.

Input/output interface 806 may comprise, for example, any type interface or interfaces that may be used for connecting to a user interface 434. As noted above, user interface 434 may comprise, for example, a display device, a computer keyboard, mouse, voice-responsive software, touch-screen, retinal control, joystick, and any other data entry or data presentation formats now or later developed. Input/output interface 806 may also be capable of receiving input from the audiologist 404 using a graphical user interface (GUI) 808 which may be displayed on a display device, as noted above.

Data transformer 804 may transform fitting system 406 based MAP data to implant-based MAP data 422. As noted above, the MAP data 422 generated by fitting system 406 may include, for example, various curves, such as a gain versus frequency curve. Data transformer 804 may package this MAP data 422 in any form suitable for use by bone conduction device 401.

Although the above embodiments were discussed with reference to providing an acoustic signal to the recipient using a speaker, it should be understood that in other embodiments, the test sound provided to the patient's good ear may be provided using other mechanisms. For example, in an embodiment, the test sound provided to the good ear may be provided using a hearing aid fitted to the recipients good ear, wherein the hearing aid may comprise a jack that allows the hearing aid to receive the test sound, such as test sound 413 of FIG. 4, from fitting system 406.

Or, in yet another embodiment, the recipient may not have a good ear, but rather one ear that is fitted with a bone conduction device 401 and another ear that is fitted with an other hearing devices, such as a middle ear implant or an inner ear implant capable of providing mechanical stimulation to a the recipient. Or, for example, the other ear may be fitted with a cochlear implant capable of providing electrical stimulation to the recipient. In such examples, a fitting system similar to the fitting system discussed above with regards to FIGS. 4-8, may be used to adjust the gains of the devices fitted to each ear of the patient so as to equalize the psychological loudness provided by each device.

Various implementations of the subject matter described, such as the embodiment of FIG. 8, may be realized using digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference herein.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for determining the psychophysical loudness of a bone conduction device, at a first frequency, wherein the bone conduction device is worn at a non-functional ear of a recipient having a functional ear, the method comprising:
   providing a first acoustic signal to the functional ear of the recipient, via a speaker, wherein the first audible signal has the frequency;
   sending a drive signal to the bone conduction device to cause the bone conduction device to deliver a second audible signal to the recipient at substantially the same time as the first audible signal is delivered, wherein the second audible signal has the first frequency, and wherein the second audible signal is generated using a gain; and
   adjusting the gain used to generate the second audible signal based on an indication of the recipient's perception of the first and second audible signals.

2. The method of claim 1, wherein adjusting the gain comprises:
   adjusting the gain based on a perceived variance in intensity between the first and second audible signals.

3. The method of claim 2, wherein adjusting the gain comprises:
adjusting the gain based on an input received from the recipient.

4. The method of claim 1, further comprising:
determining the psychophysical loudness of the bone conduction device at a plurality of frequencies.

5. The method of claim 1, further comprising:
determining map data based on the adjusted gain; and
providing the map data to the bone conduction device for use by the bone conduction device in providing stimulation to the recipient.

6. The method of claim 5, wherein the map data comprises a gain curve for use by the bone conduction in providing stimulation to the recipient.

7. A fitting system for determining the psychophysical loudness of a hearing prosthesis at a first frequency, wherein the hearing prosthesis is worn at a non-functional ear of a recipient having a functional ear, the fitting system comprising:
a speaker configured to provide a first audible signal to the functional ear of the recipient;
a bone conduction device configured to deliver a second audible signal to the recipient at substantially the same time as the first audible signal is delivered, wherein the second audible signal has the first frequency, and wherein the second audible signal is generated using a gain; and
a controller configured to adjust the gain used to generate the second audible signal based on an indication of the recipient's perception of the first and second audible signals.

8. The fitting system of claim 7, wherein the bone conduction interface is further configured to adjust the gain in response to the recipient's perceived variance in intensity in response between the first and second audible signals.

9. The fitting system of claim 7, wherein fitting system is configured to determine the psychophysical loudness of a bone conduction device at for a plurality of frequencies.

10. The fitting system of claim 7, wherein the fitting system is further configured to generate map data based on the adjusted gain for use by the bone conduction device in providing stimulation to the recipient.

11. The fitting system of claim 10, wherein the map data comprises a gain curve for use by the bone conduction in providing stimulation to the recipient.

12. The fitting system of claim 7 further comprising:
a user interface configured to display information and receive information from a user.

13. The fitting system of claim 7, wherein the interface comprises an interface configured to provide the first audible signal to the speaker in providing the first audible signal to the recipient.

14. A system for determining the psychophysical loudness of a bone conduction device, at a first frequency, wherein the bone conduction device is worn at a non-functional ear of a recipient having a functional ear, the system comprising:
means for providing a first acoustic signal to the functional ear of the recipient, via a speaker, wherein the first audible signal has the frequency;
means for delivering a second audible signal to the recipient at substantially the same time as the first audible signal is delivered, wherein the second audible signal has the first frequency, and wherein the second audible signal is generated using a gain; and
means for adjusting the gain used to generate the second audible signal based on an indication of the recipient's perception of the first and second audible signals.

15. The system of claim 14, wherein the means for adjusting the gain comprises:
means for adjusting the gain based on a perceived variance in intensity between the first and second audible signals.

16. The system of claim 15, wherein the means for adjusting the gain comprises:
adjusting the gain based on an input received from the recipient.

17. The system of claim 14, further comprising:
means for determining the psychophysical loudness of a bone conduction device at a plurality of frequencies.

18. The system of claim 14, further comprising:
means for determining map data based on the adjusted gain; and
means for providing the map data to the bone conduction device for use by the bone conduction device in providing stimulation to the recipient.

19. The system of claim 18, wherein the map data comprises a gain curve for use by the bone conduction in providing stimulation to the recipient.

* * * * *

UNITED STATES PATENT AND TRADEMARK OFFICE
CERTIFICATE OF CORRECTION

| | | |
|---|---|---|
| PATENT NO. | : 8,731,205 B2 | Page 1 of 1 |
| APPLICATION NO. | : 12/935905 | |
| DATED | : May 20, 2014 | |
| INVENTOR(S) | : John Parker | |

It is certified that error appears in the above-identified patent and that said Letters Patent is hereby corrected as shown below:

On the Title Page, Item (60) please insert the following provisional information under the Related U.S. Application Data section --Provisional application No. 61/041,185, filed on March 31, 2008.--

Signed and Sealed this
Fifth Day of August, 2014

Michelle K. Lee
*Deputy Director of the United States Patent and Trademark Office*